United States Patent [19]
Teitelbaum

[11] Patent Number: 5,807,330
[45] Date of Patent: Sep. 15, 1998

[54] ANGIOPLASTY CATHETER

[75] Inventor: George P. Teitelbaum, Los Angeles, Calif.

[73] Assignee: University of Southern California, Los Angeles, Calif.

[21] Appl. No.: 906,890

[22] Filed: Aug. 6, 1997

Related U.S. Application Data

[63] Continuation of Ser. No. 767,221, Dec. 16, 1996, abandoned.

[51] Int. Cl.$^6$ .................................................. A61M 29/00
[52] U.S. Cl. .............................. 604/96; 604/49; 606/194
[58] Field of Search .................................. 604/96, 97, 98, 604/99, 101, 49, 52, 53; 606/194, 195

[56] References Cited

U.S. PATENT DOCUMENTS

| | | |
|---|---|---|
| 5,423,742 | 6/1995 | Theron . |
| 5,634,897 | 6/1997 | Dance et al. ........................ 604/96 X |
| 5,688,234 | 11/1997 | Frisbie .................................. 604/96 X |
| 5,693,015 | 12/1997 | Walker et al. ........................... 604/96 |
| 5,695,468 | 12/1997 | LaFontaine et al. ..................... 604/96 |
| 5,713,854 | 2/1998 | Inderbitzen et al. ..................... 604/53 |

OTHER PUBLICATIONS

Theron, J. et al., "New Triple Coaxial Catheter System for Carotid Angioplasty with Cerebral Protection," *AJNR* 11:869–874 (1990).

*Primary Examiner*—John D. Yasko
*Attorney, Agent, or Firm*—Sheldon & Mak

[57] ABSTRACT

A surgical device combines an occlusion balloon to block antegrade flow of blood in the internal carotid artery during an angioplasty procedure with an exchange guidewire to facilitate the insertion of devices for performing the angioplasty procedure. The occlusion balloon/guidewire device comprises a microcatheter with a soft platinum guidewire extending therein. A silicone occlusion balloon is attached to the distal end of the microcatheter. A self-sealing valve at the distal end of the balloon permits the guidewire to extend distally therefrom. A Tuohy-Borst adapter is attached to the proximal end of the microcatheter to permit inflation of the occlusion balloon. A guidewire extension is inserted through the Tuohy-Borst adapter to seal the microcatheter once the balloon has been inflated. The Tuohy-Borst adapter is then removed over the guidewire extension member allowing the microcatheter to be utilized as an exchange guidewire.

12 Claims, 2 Drawing Sheets

ANGIOPLASTY CATHETER

CROSS-REFERENCE TO RELATED APPLICATIONS

The present Application is a Continuation of abandoned U.S. patent application Ser. No. 08/767,221, entitled "Cerebral Protection Balloon for Use in Carotid Artery Angioplasty and Stenting", filed Dec. 16, 1996, the contents of which are incorporated herein by reference in its entirety.

BACKGROUND

1. Field of the Invention

This invention relates to the field of carotid artery angioplasty, and particularly to a method and apparatus for preventing debris created by a carotid artery angioplasty procedure from entering the internal carotid artery.

2. Prior Art

The mainstay of treatment for carotid artery bifurcation atherosclerotic stenosis (in order to prevent stroke) is surgical carotid endarterectomy, in which a small incision is made in the carotid artery large enough to allow scooping out of atherosclerotic deposits within the artery wall. The incision within the artery wall is then sutured closed, allowing restoration of normal blood flow. If an endovascular means could be developed that matched the safety of surgical endarterectomy, then this procedure could be performed by a non-operative route, possibly saving thousands of dollars for each patient's hospital stay (since most patients could be discharged within one day of the endovascular procedure).

Various endovascular procedures have been proposed. For example, U.S. Pat. No. 4,650,466 issued to Luther discloses an angioplasty device comprising a woven tube of metal or plastic fibers. One or more guidewires for a stylet are attached to the woven tube for rotation and manipulation inside an artery. When the stylet or guidewires are retracted, the woven tube expands and contacts the interior, plaque-coated wall of the artery. Movement of the guidewires and expanded woven tube abrades atherosclerotic plaque from the artery to form particles that are trapped within the tube. Removal of the angioplasty device from the artery thereby removes the atherosclerotic articles from the patient.

Another endovascular approach is disclosed in U.S. Pat. No. 4,765,332 issued to Fischel et al. A pull-back atheroectomy catheter cuts and collects obstructed material as the catheter is pulled back through an atherosclerotic stenosis.

The most commonly used endovascular procedure is balloon angioplasty and stenting. Most scientific studies of carotid balloon angioplasty and stenting report a 2–6% stroke rate. A re-stenosis rate associated with surgical endarterectomy may vary between 1 and 5% and the long-term re-stenosis rate of the carotid artery following endarterectomy has been reported to be 5–11% within several years following the procedure. Dr. Jacques Theron has reported on the use of an occlusion balloon which is placed distally within the internal carotid artery during dilatation of this vessel in order to prevent stroke related to carotid artery angioplasty. He reports a nearly zero percent stroke rate when this technique is used. The problem with the use of his triaxial balloon technique is that the balloon cannot be kept inflated continuously in between pre-dilatation of the atherosclerotic stenosis and stenting of the vessel. If a balloon catheter could be kept inflated within the internal carotid artery and still be used as an exchange guidewire to permit the exchange of multiple different catheter devices to complete balloon dilatation and stenting of the internal carotid artery, then this would be a major advance in the technique.

SUMMARY

The present invention provides a device which combines an occlusion balloon to block antegrade flow of blood in the internal carotid artery during an angioplasty procedure with an exchange guidewire to facilitate the insertion of devices for performing the angioplasty procedure. The occlusion balloon/guidewire device of the present invention comprises a microcatheter with a soft platinum guidewire extending therein. A silicone occlusion balloon is attached to the distal end of the microcatheter. A self-sealing valve at the distal end of the balloon permits the guidewire to extend distally therefrom. A Tuohy-Borst adapter is attached to the proximal end of the microcatheter to permit inflation of the occlusion balloon. A guidewire extension is inserted through the Tuohy-Borst adapter to seal the microcatheter once the balloon has been inflated. The Tuohy-Borst adapter is then removed over the guidewire extension member allowing the microcatheter to be utilized as an exchange guidewire.

FIGURES

DESCRIPTION

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

Figure 1:
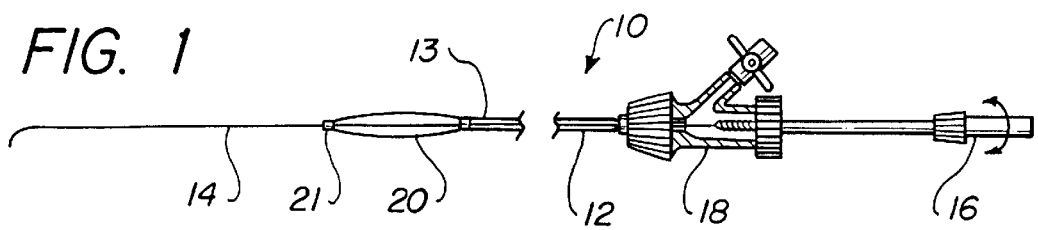
FIG. 1 is a side elevation view of an occlusion balloon/guidewire device according to the present invention.

The occlusion balloon/guidewire device 10 of the present invention is shown generally in FIG. 1. The microcatheter 12 has a maximum diameter of approximately 0.035 inch, i.e, slightly less than 3-French in greatest outer diameter. It is approximately 300 cm long. A 0.010 inch to 0.014 inch (OD)

soft platinum balloon/guidewire device 14 extends from the distal tip 13 of the microcatheter 12. This permits use of a steering device 16 on the more proximal portion of the catheter so that the soft platinum wire tip can be navigated past a tight carotid stenosis using digital roadmap imaging. Occlusion balloon 20 is disposed at the distal end of catheter 12. The balloon 20 is made out of high compliance silicone and is designed to inflate with low pressures (less than 1 atmosphere). A self-sealing rubberized valve 21 seals the distal end of balloon 20 around guidewire 14.

Figure 2:
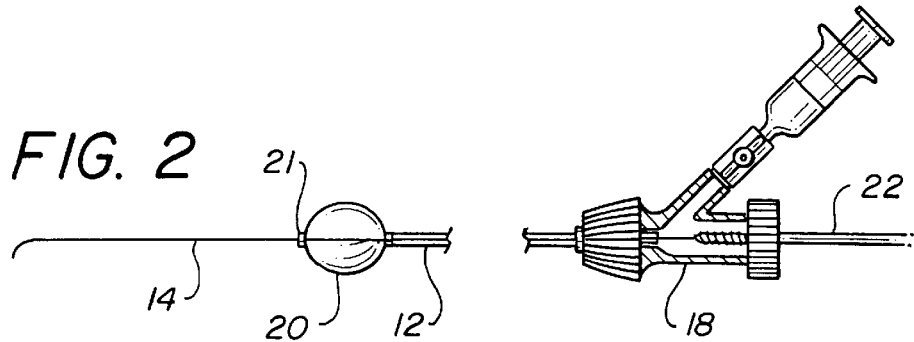
FIG. 2 illustrates inflation of the occlusion balloon of the device of FIG. 1.
Figure 3:
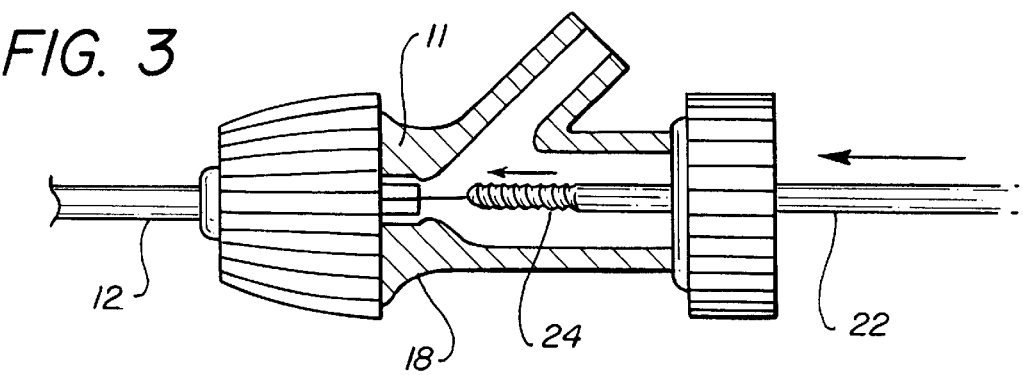
FIG. 3 is an enlarged view illustrating attachment of the guidewire extension member of the present invention.
Figure 4:
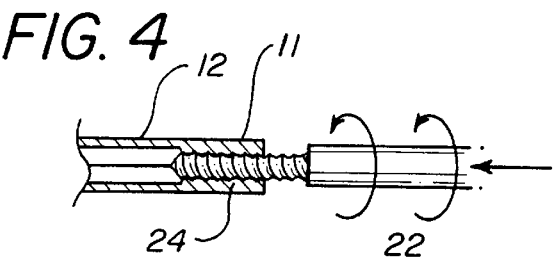
FIG. 4 illustrates attachment of a threaded embodiment of the guidewire extension member.
Figure 5:
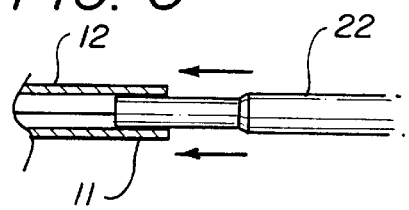
FIG. 5 illustrates attachment of a friction-fit embodiment of the guidewire extension member.
Figure 6:
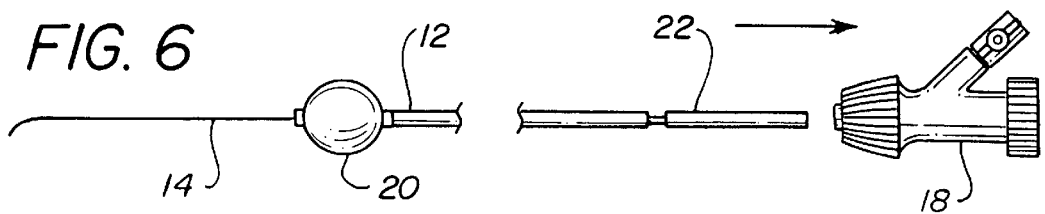
FIG. 6 illustrates removal of the Tuohy-Borst adapter to permit the device of the present invention to be used as an exchange guidewire.

Referring next to FIG. 2, a removable Tuohy-Borst adapter 18 is disposed at the proximal portion of the device 10 for inflating the distal balloon tip 20 of the catheter. Once inflated with dilute contrast solution, the balloon is kept inflated by the insertion of a proximal 0.035 inch (OD) stainless steel extension 22 of the guidewire as more clearly shown in FIG. 3. In one embodiment, as shown in FIG. 4, the extension member has a threaded segment 24. The extension member is passed through the Tuohy-Borst adapter and inserted into the proximal end 11 of the occlusion balloon/guidewire device 10. The proximal end 11 of this device has a threaded inner lumen so that the guidewire extension device can be threaded into the occlusion balloon/guidewire device, thus sealing the contrast solution within its central lumen and keeping the balloon 20 inflated. The Tuohy-Borst adapter may then be loosened and removed from the occlusion balloon/guidewire device with the balloon still left inflated. Thus, with the Tuohy-Borst adapter removed, this catheter, together with its inflated balloon, can now be used as an exchange guidewire. Alternatively, as shown in FIG. 5, the distal end of guidewire extension member 22 may have a smooth exterior with an OD >0.014 inch but <0.035 inch for a press fit within the lumen of catheter 12. Once inserted into the proximal microcatheter lumen, where it would lock in by friction, inflation of the distal balloon 20 is maintained.

Figure 7:
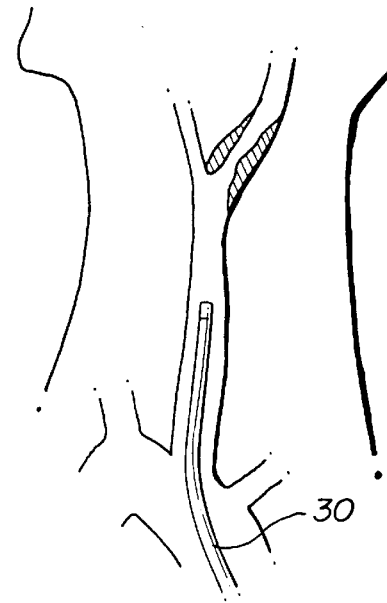
FIG. 7 illustrates insertion of a guiding catheter into the common carotid artery.

FIGS. 7–11 illustrate the use of device 10 in a carotid artery angioplasty procedure. The patient is systemically heparinized during the procedure. Via the femoral approach, a long 9-French access sheath is inserted through the common femoral artery and is advanced into the abdominal aorta. Through this long 9-French sheath, a 5–7 French selective catheter is used to access the common carotid artery on he side of carotid artery stenosis. Through this catheter, contrast arteriography of the carotid bifurcation is performed demonstrating the exact location of the narrowed area of the carotid artery. Next, over a 0.035 inch OD exchange guidewire, the selective catheter is exchanged for a 9-French guiding catheter 3. The 9-French catheter is advanced to the distal portion of the common carotid artery as shown in FIG. 7. There, using digital roadmap imaging, the balloon occlusion/guidewire device 10 is coaxially inserted through the 9-French guiding catheter.

Figure 8:
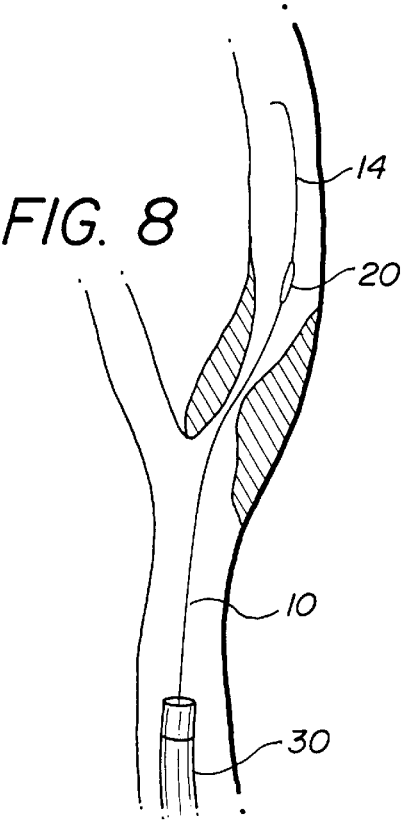
FIG. 8 illustrates insertion of the occlusion balloon/guidewire device of the present invention into the site of an arterial stenosis.

With reference now to FIG. 8, the soft steerable platinum guidewire tip 14 is used to advance device 10, past the area of stenosis into the more distal cervical portion of the carotid artery. In this location, the balloon tip 20 of the balloon occlusion/guidewire device is inflated with dilute contrast through the Tuohy-Borst device attached to its proximal end. Once it is determined that there is antegrade flow arrest within the internal carotid artery, the 0.035 inch guidewire extension 22 is inserted into the proximal end of the device and screwed or pressed into place, thus maintaining balloon inflation. The Tuohy-Borst device is then removed from the proximal portion of the balloon occlusion/guidewire device.

Figure 9:
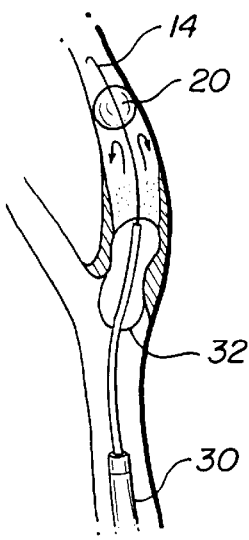
FIG. 9 illustrates inflation of the occlusion balloon and deployment of a balloon catheter at site of the arterial stenosis.
Figure 10:
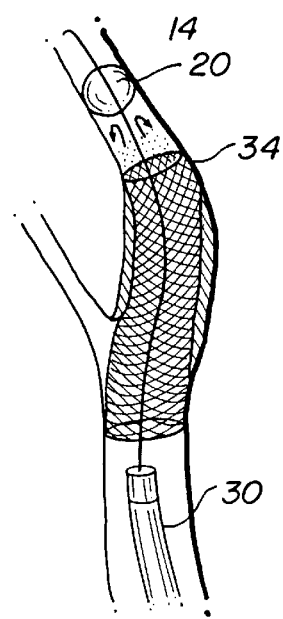
FIG. 10 illustrates deployment of an endovascular stent at the site of the arterial stenosis.

At this point, as shown in FIG. 9, a balloon angioplasty catheter 32 is inserted through the 9-French guiding catheter 30 over the balloon occlusion/guidewire device 10 to pre-dilate the carotid stenosis. Alternatively, a balloon catheter with a Palmaz stent mounted on its uninflated balloon could be used, or a Wall stent device could be advanced over device 10 to the area of stenosis for dilatation and stenting of the lesion. By whichever procedure is utilized, stent 34 is deployed at the area of stenosis as shown in FIG. 10. Debris created by the balloon angioplasty and stent placement procedure is trapped proximally to occlusion balloon 20.

Figure 11:
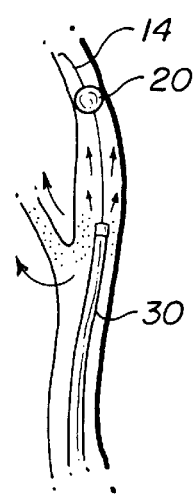
FIG. 11 illustrates flushing of the angioplasty site prior to the deflation of the occlusion balloon.

Following dilatation of the stenosis and deployment of the endovascular stent 34, the stent delivery device is removed from the exchange guidewire and vigorous flushing of the angioplasty and stenting site is performed as illustrated in FIG. 11. A large volume of saline is injected through the 9-French guiding catheter, which flushes any microscopic debris created by the angioplasty and stenting into the ipsilateral external carotid artery. Next, the guidewire extension device 22 is unscrewed from the proximal end of device 10, thus allowing deflation of the silicone balloon and also restoring antegrade flow within the internal carotid artery. The balloon occlusion/guidewire device together with the 9-French guiding catheter is then removed from the groin sheath and the groin sheath is removed from the patient, following reversal of systemic heparinization. Hemostasis in the inguinal area is effected by manual compression.

It will be recognized that the above described invention may be embodied in other specific forms without departing from the spirit or essential characteristics of the disclosure. Thus, it is understood that the invention is not to be limited by the foregoing illustrative details, but rather is to be defined by the appended claims.

We claim:

1. A device for crossing a stenotic intravascular lesion, for occluding blood flow downstream from the intravascular lesion and for use as an exchange guidewire, the device comprising:

a balloon catheter having a catheter body with a proximal end and a distal end, an inflation balloon attached at or near the distal end of the catheter body, and an inflation conduit within the catheter body connecting the inflation balloon with the proximal end of the balloon catheter;

an adapter for inflating the inflation balloon, the adapter configured to be removably connectable to the proximal end of the balloon catheter; and a extension member having a distal end configured to be removably connectable to the proximal end of the balloon catheter for sealing the proximal end of the inflation conduit;

wherein the device is configured such that, after inflating the inflation balloon, the inflation of the inflation balloon is maintained by connecting the extension member to the proximal end of the inflation conduit when the adapter is removed.

2. The device of claim 1, wherein the adapter is a Tuohy-Borst adapter.

3. The device of claim 1, wherein the distal end of the extension member has an external thread and the proximal end of the inflation conduit has an internal thread allowing the distal end of the extension member and proximal end of the inflation conduit to be threadedly connected to each other.

4. The device of claim 1, wherein the distal end of the extension member has a substantially smooth external surface and the proximal end of the inflation conduit has a substantially smooth internal surface, and where the external surface and internal surface are configured to sealing connect by friction.

5. A method of performing an intravascular procedure comprising the steps of:
   (a) providing a catheter according to claim 1;
   (b) inserting the catheter into a blood vessel and advancing the catheter to a selected position within the blood vessel;
   (c) inflating the inflation balloon to occlude blood flow in the blood vessel;
   (d) connecting the extension member to the proximal end of the inflation conduit; and
   (e) removing the adapter.

6. The method of claim 5, additionally comprising the step of placing a stent intravascularly after the inflating step.

7. The method of claim 5, additionally comprising the step of flushing debris from the blood vessel after the inflating step.

8. The method of claim 5, additionally comprising the step of disconnecting the extension member from the proximal end of the inflation conduit, thereby deflating the inflation balloon and restoring blood flow within the blood vessel.

9. A method of performing an intravascular procedure comprising the steps of:
   (a) providing a device including, i) a balloon catheter having a catheter body with a proximal end and a distal end, an inflation balloon attached at or near the distal end of the catheter body, and an inflation conduit within the catheter body connecting the inflation balloon with the proximal end of the balloon catheter; ii) an adapter for inflating the inflation balloon, the adapter configured to be removably connectable to the proximal end of the balloon catheter; and iii) a extension member having a distal end configured to be removably connectable to the proximal end of the balloon catheter for sealing the proximal end of the inflation conduit; wherein the device is configured such that, after inflating the inflation balloon, the inflation of the inflation balloon is maintained by connecting the extension member to the proximal end of the inflation conduit when the adapter is removed, thereby allowing the catheter body to function as an exchange guidewire while inflation of the inflation balloon is maintained;
   (b) inserting the catheter into a blood vessel and advancing the catheter to a selected position within the blood vessel;
   (c) inflating the inflation balloon to occlude blood flow in the blood vessel;
   (d) connecting the extension member to the proximal end of the inflation conduit; and
   (e) removing the adapter.

10. The method of claim 9, additionally comprising the step of placing a stent intravascularly after the inflating step.

11. The method of claim 9, additionally comprising the step of flushing debris from the blood vessel after the inflating step.

12. The method of claim 9, additionally comprising the step of disconnecting the extension member from the proximal end of the inflation conduit, thereby deflating the inflation balloon and restoring blood flow within the blood vessel.

* * * * *